(12) United States Patent
Soenksen et al.

(10) Patent No.: US 11,211,170 B2
(45) Date of Patent: *Dec. 28, 2021

(54) SECOND OPINION NETWORK (71) Applicant: Leica Biosystems Imaging, Inc., Vista, CA (US)

(72) Inventors: Dirk G. Soenksen, Carlsbad, CA (US); Kathy Zirker-Smith, Mill Valley, CA (US); Ole Eichhorn, Westlake Village, CA (US)

(73) Assignee: Leica Biosystems Imaging, Inc., Vista, CA (US)

( * ) Notice: Subject to any disclaimer, the term of this patent is extended or adjusted under 35 U.S.C. 154(b) by 291 days.

This patent is subject to a terminal disclaimer.

(21) Appl. No.: 15/912,428

(22) Filed: Mar. 5, 2018

(65) Prior Publication Data

US 2018/0197639 A1 Jul. 12, 2018

Related U.S. Application Data

(63) Continuation of application No. 14/060,522, filed on Oct. 22, 2013, now Pat. No. 9,910,961, which is a
(Continued)

(51) Int. Cl.
*G16H 80/00* (2018.01)
*G16H 30/20* (2018.01)
*G16H 50/50* (2018.01)

(52) U.S. Cl.
CPC .............. *G16H 80/00* (2018.01); *G16H 30/20* (2018.01); *G16H 50/50* (2018.01)

(58) Field of Classification Search
CPC ........ G16H 80/00; G16H 50/50; G16H 30/20; G06F 19/321
See application file for complete search history.

(56) References Cited

U.S. PATENT DOCUMENTS

2002/0001402 A1* 1/2002 Berliner ................. G01N 15/05
382/133
2003/0061285 A1* 3/2003 Usui ................... G09B 19/0038
709/205
(Continued)

OTHER PUBLICATIONS

Su et al., Managing and distributing remote sensing images based on metadata and microimage, 2003, Proceedings of SPIE, vol. 4898, pp. 49-56. (Year: 2003).*

*Primary Examiner* — Christopher L Gilligan
(74) *Attorney, Agent, or Firm* — Knobbe, Martens, Olson & Bear, LLP (57) ABSTRACT

Systems and methods are provided to facilitate consultations between a referral source (e.g., labs, pathologists and patients) and a consultant (e.g., pathologist, radiologist, or other digital image analyst). Links between the various referral sources and consultants are established through a scanning center via a data communication network such as the Internet. The referral source sends a slide to the scanning center where the corresponding digital slide is posted for review and analysis by the consultant. Upon completion of the analysis and report, a digital slide conference is conducted through the scanning center that provides a venue for direct communication regarding the consultation. The scanning center may also facilitate payment from the referral source to the consultant.

21 Claims, 2 Drawing Sheets

Related U.S. Application Data continuation of application No. 12/110,185, filed on Apr. 25, 2008, now Pat. No. 8,565,498.

(60) Provisional application No. 60/914,571, filed on Apr. 27, 2007.

(56) References Cited

U.S. PATENT DOCUMENTS

| | | | |
|---|---|---|---|
| 2004/0034550 A1* | 2/2004 | Menschik | G16H 70/20 705/3 |
| 2004/0139222 A1* | 7/2004 | Slik | G16H 10/60 709/236 |
| 2004/0141661 A1* | 7/2004 | Hanna | G06Q 10/10 382/305 |
| 2006/0025670 A1* | 2/2006 | Kim | G16H 80/00 600/407 |
| 2006/0159367 A1* | 7/2006 | Zeineh | G06T 7/0012 382/276 |
| 2006/0195339 A1* | 8/2006 | Backhaus | G06Q 10/06 705/2 |
| 2007/0162305 A1* | 7/2007 | Miller | G06Q 10/00 705/2 |
| 2007/0201864 A1* | 8/2007 | Shinkai | G11B 27/034 396/429 |

\* cited by examiner

SECOND OPINION NETWORK

RELATED APPLICATION

The present application is a continuation of U.S. patent application Ser. No. 14/060,522, filed on Oct. 22, 2013, which is a continuation of U.S. patent application Ser. No. 12/110,185, filed on Apr. 25, 2008, and issued as U.S. Pat. No. 8,565,498, which claims priority to U.S. Provisional Patent App. No. 60/914,571, filed on Apr. 27, 2007—the entireties of all of which are hereby incorporated herein by reference.

BACKGROUND

Field of the Invention

The present invention generally relates to medical diagnosis and more specifically relates to providing a network of pathologists that render second opinions on medical diagnoses.

Related Art

In the current state of medical diagnoses, pathologists may feel uncomfortable rendering a final diagnosis on a difficult case and/or a case outside his or her area of expertise. Such a pathologist may want a second opinion and not be able to get one from within the pathologist's practice group or medical organization. Alternatively, a patient may simply ask for a second opinion.

In these situations, a pathologist typically sends one or more of the patient's glass slides (with a specimen on it) to a consulting pathologist, typically someone with whom the pathologists or the pathologist's lab has a standing relationship, to receive the second opinion. The turnaround time for a second opinion can be extremely slow, weeks even months for the result (e.g., the more famous/expert the consulting pathologist, the longer the wait), particularly in cases where the consulting pathologist lives in another country and slides are held up in customs. Eventually, the provider of the second opinion sends back a report (or perhaps delivers the report orally via telephone) and hopefully also sends back the glass slide. A common problem today is that original slides never get returned.

The consulting pathologist who renders the second opinion may bill the referring pathologist for the consultation or may submit billing to an insurance carrier directly. The carrier may reimburse if they consider the second opinion medically necessary. Carriers also may choose not to reimburse the pathologist who renders the second opinion, which discourages willingness to provide second opinions.

Additionally, a patient may want a second opinion but not feel comfortable requesting one, or a patient may request a second opinion and be denied. For example, the patient's primary care physician may conclude that a second opinion is not necessary or the insurance carrier may deny the requested second opinion. In any case, when a patient is denied a requested second opinion the patient has few options.

Therefore, what is needed is a system and method that overcomes these significant problems found in the conventional systems as described above.

SUMMARY

Described herein are systems and methods that establish a network of known pathologists who provide consultations to labs, pathologists and patients, using digital pathology. Advantageously, the systems and methods described herein provide an infrastructure that facilitates formal and information second opinions, provides subject matter expertise that is not available to a particular practice group or medical organization, allows for workload balancing, skill-building, education, and satisfaction of patient requests. An additional advantage is that highly regarded experts who are recognized as the leading practitioners in their respective fields are made accessible to small practice groups and individuals that would otherwise not be able to consult with such an expert.

In one embodiment, the system includes a network of participating consultants and referral sources. For example, consultants may include individuals, medical groups and educational facilities, just to name a few. Referral sources may include doctors, pathologists, labs, medical groups, hospitals, educational facilities, and individual patients as well as other referral sources. The participating referral sources are provided with mailers for glass slides or alternatively the referral sources are provided with digital slide scanners or access to digital slide scanners.

The physical slide is sent from the referral source (e.g., doctor, lab, patient) to a scanning center for creation of a digital slide and then the physical slide is returned to the referral source. Alternatively, if the referral source has a digital slide scanner or has access to a digital slide scanner (e.g., at a community health facility or the like), the digital slide is electronically sent to the scanning center. The scanning center then makes the digital slide available for viewing by a consulting pathologist via a communication network such as the Internet.

Advantageously, the consulting pathologist can view and analyze the digital slide at his or her convenience and make a diagnosis. Subsequently, a digital slide conference (e.g., an audio-video conference) is hosted by the scanning center to facilitate information exchange between the consulting pathologist and referral source (doctor, pathologist, patient, or any combination).

Significant benefits are realized from the described systems and methods for a second opinion network. Some of the benefits include real-time discussions between the expert pathologist(s) and the referral source via digital slide conferencing; establishing turn around time ("TAT") requirements for participation; original glass slides are not lost (or never returned); and simplified economics for consultants (e.g., patient pays directly for requested second opinion). Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a second opinion network that links referral sources (e.g., referring pathologists, patients) and consulting pathologists to facilitate second opinions regarding analysis of digitized microscope slide specimens. For example, one method as disclosed herein allows for a referral source to scan a microscope slide into a digital format and then send the digital slide to a scanning center where it is hosted and made available to one or more consultants via a data communication network. After an analysis has been completed by the one or more consultants, a digital slide conference between the referral source and the one or more consultants is hosted by the scanning center via the data communication network. The scanning center may also facilitate payment to the consultant.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
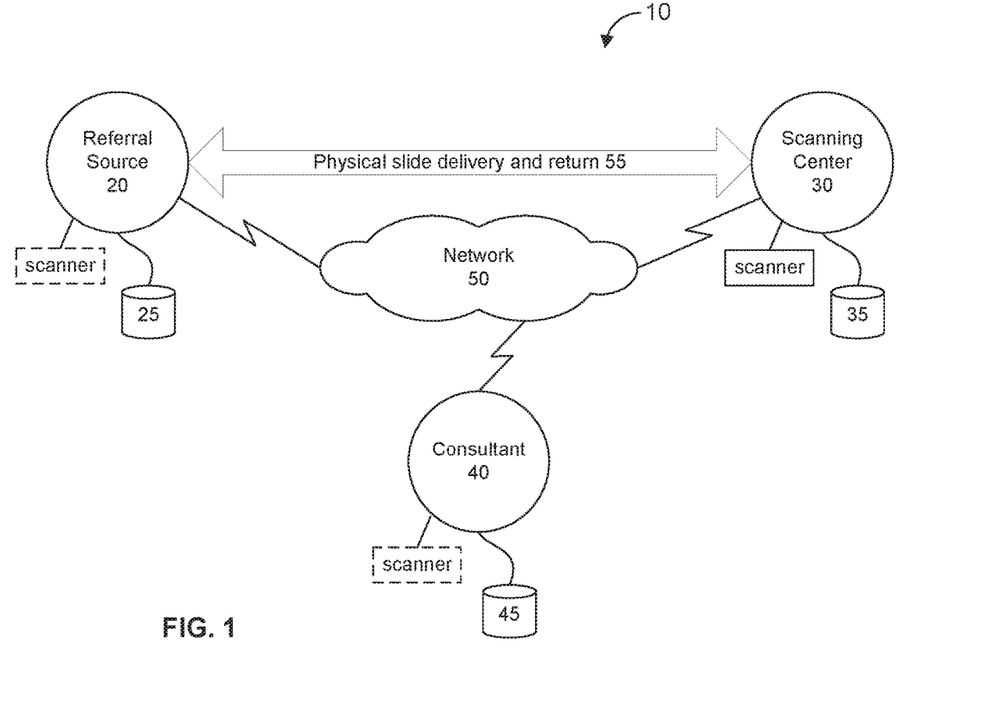
FIG. 1 is a network diagram illustrating an example system for a second opinion network according to an embodiment of the invention.

FIG. 1 is a network diagram illustrating an example system 10 for a second opinion network according to an embodiment of the invention. In the illustrated embodiment, the referral source 20, scanning center 30, and consultant 40 each have respective data storage areas 25, 35, and 45 and are all connected via a communication network 50. The referral source 20 originates the referral for a second opinion. This may be at the direction of a lab, the attending physician, or at the request of the patient. The referral source 20 can send the glass slide to a scanning center 30 via a physical delivery and return infrastructure 55 or it can scan the slide itself and then send a digital slide to the scanning center 30 via the network 50. In one embodiment, the referral source 20 can send metadata information regarding the digital slide to the scanning center 30 and store the native digital slide image data in its local data storage 25. At some subsequent time (e.g., during off peak network usage hours) the referral source can send the native digital slide image (which may be several gigabytes in size) to the scanning center 30.

The scanning center 30 scans the physical slide and returns it to the referral source 20 (if it receives the original physical slide). This advantageously eliminates the problem of lost or never returned slides that is common today. Whether receiving a physical slide or a digital slide from the referral source 20, once the scanning center 30 has the digital slide, it stores the digital slide and its respective metadata information and makes it available for viewing by the consultant 40 via the network 50. The scanning center 30 may also notify the consultant 40 that the digital slide is available for viewing. Such notice can be accomplished by electronic communication (e.g., email, text message, chat message, or the like) or by more traditional means including phone, fax, and regular mail.

In one embodiment the scanning center 30 initially receives metadata for a digital slide and uses the metadata, which includes a reference to the location of the digital slide image stored in data storage 25 at the referral source device 20, to facilitate the rendering of the second opinion. In such an embodiment, the scanning center 30 may subsequently receive the digital slide image for storage in the data storage area 35 in association with the related metadata. Storage at the scanning center is advantageous because the scanning center is configured for data redundancy and backup. The scanning center 30 is also configured for high bandwidth data communications so it can facilitate rapid viewing of the large amounts of data typically associated with high image quality digital slides. For example, during a digital slide conference the scanning center 30 may provide multiple gigabytes of data simultaneously to several remote viewers (e.g., referral source devices and consultant devices).

The scanning center data storage area 35 is preferably configured to manage and store digital slide metadata and digital slide image data for all of the digital slides in the second opinion network. For digital slides that have the image data stored elsewhere (e.g., in local storage at the referral source device) the data storage area 35 includes a reference to the native digital slide image data (e.g., a link or other electronic address). In this fashion the scanning center 30 operates as a central database 35 of all of the digital slides and related information (metadata) in the network.

The consultant 40 views the digital slide via the network 50, conducts an examination of the digital slide, renders a diagnosis and then delivers a report to the referral source 20. The report can be delivered in the context of a digital slide conference that allows the consultant 40 to walk through the analysis while both the consultant 40 and the referral source 20 are simultaneously viewing the digital slide hosted by the scanning center 30 via the network 50. In one embodiment, the digital slide conference may include the patient. The digital slide conference can be recorded and made part of the patient's medical file. Alternatively, a written report or other report can be delivered to the referral source.

In one embodiment, the scanning center 30 also includes decision support tools that can be used by a consultant when analyzing a digital slide image. Such tools may assist the consultant with making a diagnosis or may provide specific digital slide image related information such as cell count or other information that may be the result of clinical algorithms processed against the digital slide image data.

The scanning center 30 may also store a profile for each consultant that allows the consultant to maintain personal and professional information that can be reviewed by potential referral sources when making a decision of which consultant to engage for slide analysis (whether second opinion or original analysis). In one embodiment, a profile may include references to prior work performed by the consultant with links to digital slides previously analyzed. Additional collections of information may also be provided by the consultant and stored in data storage area 35.

The second opinion system establishes a network of pathologists who provide second opinions for doctors or labs who want them and also for patients who request them. Participating pathologists may participate because they want to handle secondary consults for financial or clinical interests. Advantageously, patients who want a second opinion can pay for their consultation and feel confident that they were tapping into an expert network and the second opinion was unbiased by the interests of an insurance carrier. Similarly, labs who want a second opinion also feel confident because they are tapping into an expert network.

One particular advantage of using digital pathology for the second opinion network is that it facilitates a quicker second opinion (e.g., by establishing turn around time ("TAT") requirements for participation). Additionally, the use of digital pathology also enables real-time discussion between the referral source 20 and the consultant 40 (e.g., an expert pathologist) via digital slide conferencing. This real-time discussion has the added benefit of facilitating the transfer of knowledge from the experts to other medical practitioners.

Another significant advantage of the second opinion network system is that it provides easy access for labs and patients to leading pathologists in a variety of fields. These leading pathologist are enabled through the second opinion network to efficiently and cost effectively provide second opinions outside of existing medical practice groups to improve the quality of diagnostic results, further educate members of the practice group, and reduce the economic influence and impact of medical insurance carriers. For example, participating pathologists are provided with an additional source of revenue and are also allowed greater access to clinically-interesting cases which may further an individual pathologist's notoriety and recognition as an expert in a particular field. Additionally, just being selected as a reviewing expert on high profile cases or very difficult cases can provide a certain amount of prestige to the expert.

As mentioned above, the initial step in the second opinion process is for the physical slide to get scanned to create a digital slide. The scanning can take place at the referral source 20 (e.g., lab, doctor office, hospital, etc.), at a third party scanning center 30, or even at the consultant 40. In one embodiment, a third party scanning center 30 may provide referral sources 30 with postage paid mailer envelopes in which physical slides can be sent to the scanning center 30 or to the consultant 40. For example, experts who provide a large volume of second opinions or who operate their own lab may prefer to have their own digital scanner.

The scanning device can be any of a variety of digital scanners, including conventional image tiling devices or the faster and higher quality linear array based devices such as the patented ScanScope® device produced by Aperio Technologies, Inc. described in U.S. Pat. No. 6,711,283 which is incorporated herein by reference in its entirety.

Once the digital slide is available for viewing at the scanning center 30 (when the physical or digital slide is not sent directly to the consultant), the scanning center 30 notifies the consultant 40 that the slide is ready to be analyzed. In one embodiment, the scanning center 30 may facilitate the selection of the expert consultant 40, for example if the referral source 20 has not identified or pre-arranged who the consultant 40 is to be. If the consultant 40 has been selected by the referral source 20 (e.g., patient or referring physician/pathologist) the scanning center 30 notifies the identified consultant 40. The consultant 40 then accesses the scanning center 30 via the network 50 to review the digital slide within an agreed-upon time frame.

In one embodiment, certain security measures may be in place at the scanning center that may, for example require the consultant 40 to provide a user name and password in order to gain access to the digital slide to be reviewed. The consultant 40 may have an account with the scanning center 30 such that a series of digital slides may be presented to the consultant 40 upon logging in to the scanning center 30. The scanning center may also include certain administrative software utilities to allow the expert to make notes (hand written and scanned, voice recordings, or other) that are stored in a data storage area 35 at the scanning center 30 in association with the related digital slide. The administrative utilities may also provide the referral source 20 with the ability to provide a context for the digital slide, with background, demographic or other information that may be helpful to the consultant 40 when reviewing the digital slide. In one embodiment, the patient's entire medical file may accompany the digital slide that is provided to the consultant 40.

In one embodiment, the scanning center is a special site that support high bandwidth communications, so as to facilitate simultaneous access, including digital slides conferences, to multiple digital slides by multiple consultants, without degradation in viewing performance.

In one embodiment, the referral source 20 scan the physical (glass) slide and the resulting digital slide is stored at the referral source 20, where it is accessed via the data communication network 50 by the consultant 40. In this case, the digital slide is not transported to the scanning center 30, although (meta) data about the digital slide may be transported to the scanning center for incorporation into the database at the scanning center that keeps track of all digital slides in the system 10.

After the review and analysis is complete, the consultant 40 then discusses the case with the referral source 20, e.g., through a phone call or a digital slide conferencing session hosted by the scanning center 30 that includes both audio and visual information. For example, the scanning center 30 (or consultant 40) could host a digital slide conference during which the consultant 40 would review the findings with the referral source 20, e.g., a referring pathologist and/or patient. This conference could be recorded and stored in data storage areas 25, 35 or 45 (or any combination of these) for augmenting the patient's medical file. Additionally, a detailed or summary report can be generated by the scanning center 30.

In one embodiment, a patient may request a second opinion from their attending medical professional (e.g., surgeon, oncologist, internist, or doctor). If the requested second opinion is denied (e.g., has already been performed by the lab or medical group, is medically unnecessary, would not be paid for by the insurance carrier, etc.), the patient can decide to pay directly for the second opinion. Accordingly, the doctor (referral source 20) sends the physical or digital slide to the scanning center 30 or consultant 40 so that the second opinion can be rendered. The digital slide conference can then take place to deliver the second opinion to the referral source 20 (e.g., doctor and patient). The patient may make payment directly to the scanning center 30 who in turn makes payment to the consulting pathologist 40. The patient may also make payment directly to the consultant 40 or to the attending medical professional who in turn makes payment to the consultant 40.

Advantageously, for the referral source 20 that is requesting the second opinion, the second opinion network provides easy access to a network of leading experts that operate as consultants 40. The second opinion network, through its digital slide conferences also provides a way for a referring medical professional to discuss the findings of the consultant 40, thus improving the medical professional's diagnosis skills. For the consultant 40, providing an increased volume of second opinion consultations without billing hassles has economic benefits and may also increase notoriety for the consultant 40. For patients, benefits include increased confidence that the patient is accessing the skills of a leading expert to ensure that the diagnosis is correct and the peace of mind that comes from getting that opinion quickly.

Figure 2:
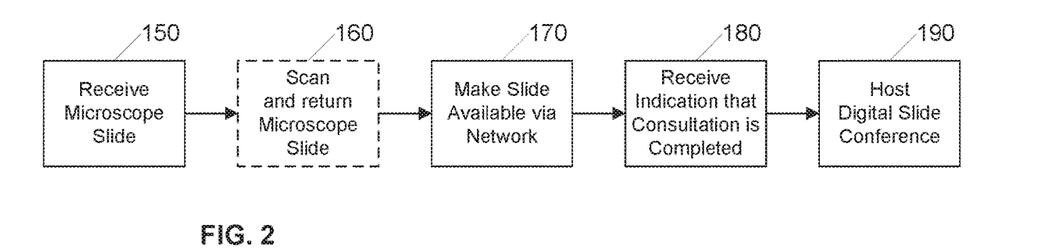
FIG. 2 is a flow diagram illustrating an example process for implementing a second opinion network according to an embodiment of the invention.

FIG. 2 is a flow diagram illustrating an example process for implementing a second opinion network according to an embodiment of the invention. The illustrated process may be carried out by a scanning center such as previously described with respect to FIG. 1. Initially, in step 150 the scanning center receives the microscope slide. If the slide is a physical (glass) slide then in optional step 160 the scanning center digitally scans the physical slide and then returns the physical slide to the referral source. Advantageously, using digital pathology and centralizing the scanning function results in a significant increase in physical slides being returned to the referral source.

Once the scanning center has the digital slide, it makes the slide available to one or more consultants via a data network, as shown in step 170. For example, a consultant may login to the scanning center via the Internet and review the digital slide. Certain security measures may be taken at the scanning center to ensure privacy.

Next, in step 180 the scanning center receives an indication that the consultation is complete. This indication may be the completion of an analysis report or something similar. Or the indication may be an email or other message. The indication may also be in some other form capable of being received and processed by the scanning center such as a fax, phone call, selection of a radio button or other item via a user interface. Many alternatives for providing an indication of the analysis being complete are available as will be understood by those skilled in the art.

Once the consultant has completed the second opinion analysis, the scanning center in step 190 hosts a digital slide conference between the consultant and the referral source (e.g., patient, doctor, lab, etc.). The digital slide conference can be an audio-video conference that takes place over a data communication network that interconnects the referral source, the scanning center, and the consultant. The digital slide conference may be recorded and inserted into the patient's file. If the referral source and the consultant decide not to conduct a digital slide conference, the consultant may deliver a report to the referral source directly, or indirectly via the scanning center.

Figure 3:
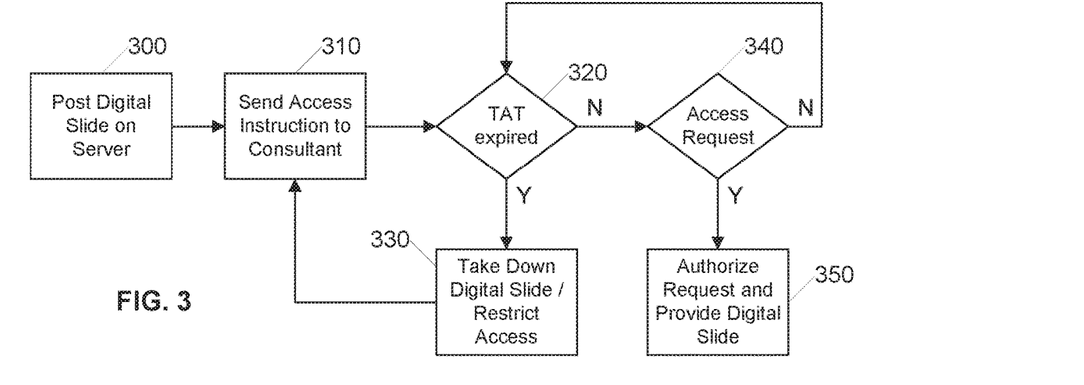
FIG. 3 is a flow diagram illustrating an example process for facilitating a second opinion analysis according to an embodiment of the invention.

FIG. 3 is a flow diagram illustrating an example process for facilitating a second opinion analysis according to an embodiment of the invention. The illustrated process may be carried out by a scanning center such as previously described with respect to FIG. 1. Initially, in step 300 the scanning center posts the digital slide on a server that is accessible by the consultant, for example via the Internet. Next, in step 310 the scanning center sends the access information to one or more consultants. The access information may be in the form of a link or it may be a simple notice that the consultant has a digital slide awaiting review.

In one embodiment, more than one consultant may be sent the access information and only the first to respond is engaged for the second opinion. Alternatively, more than one consultant may be sent the access information and only the first to complete the review and analysis is engaged for the second opinion. Introducing competition in this fashion has the desired effect of decreasing TAT for second opinions.

Next, in step 320 the scanning center determines if the turn around time has expired for the review and analysis of the digital slide that was sent to the consultant. If the TAT has expired, then the scanning center may take down the digital slide from the server. Alternatively, the scanning center may revoke access for the first consultant and circle back to step 310 and send an access instruction to a subsequent consultant.

If the TAT has not expired, and the scanning center receives an access request, as determined in step 340, then the request from the consultant is authorized in step 350 and the digital slide is provided to the consultant for analysis. In one embodiment, the digital slide is only displayed on a monitor at the location of the consultant and is not downloaded to the consultant work station for offline viewing or storage. Alternatively, the digital slide may be downloaded to the consultant workstation for local storage and offline viewing.

Figure 4:
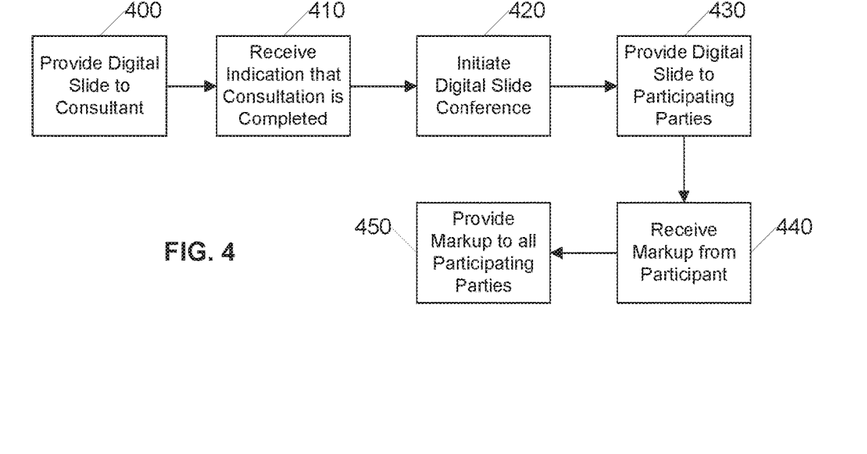
FIG. 4 is a flow diagram illustrating an example process for facilitating a digital slide conference according to an embodiment of the invention.

FIG. 4 is a flow diagram illustrating an example process for facilitating a digital slide conference according to an embodiment of the invention. The illustrated process may be carried out by a scanning center such as previously described with respect to FIG. 1. Initially, in step 400 the scanning center provides the digital slide to the consultant, either by displaying the slide on a screen at the consultant workstation or by downloading the digital slide to the consultant workstation as previously described. Next, in step 410 the scanning center receives an indication that the consultation/analysis is completed and then in step 420 the scanning center initiates a digital slide conference between the referral source and the consultant. Advantageously, the conference may be an audio-visual conference where the referral source and the consultant simultaneously view the digital slide on their respective workstations with an audio connection to allow for discussion while viewing the slide. In step 430 the scanning center provides the digital slide to each participating party so that all parties can view the slide simultaneously.

In step 440, the scanning center receives a markup from one of the participants in the digital slide conference. In one embodiment, the consultant may lead the digital slide conference and therefore the consultant may make annotations on the digital slide at the consultant's workstation. The scanning center receives these types of markups (e.g., annotations) and then propagates the markups to the displays of each of the other participants. For example, the consultant may circle a particular feature in the digital slide and that same circle would then appear around the particular feature on the screen at the referral source. The scanning center is configured to host the digital slide conference and may also include features that allow the various participants to take control of the session, to make private annotations, and the like. Additionally, the scanning center is configured to record the digital slide conference, which then may become part of the patient's medical record.

Figure 5:
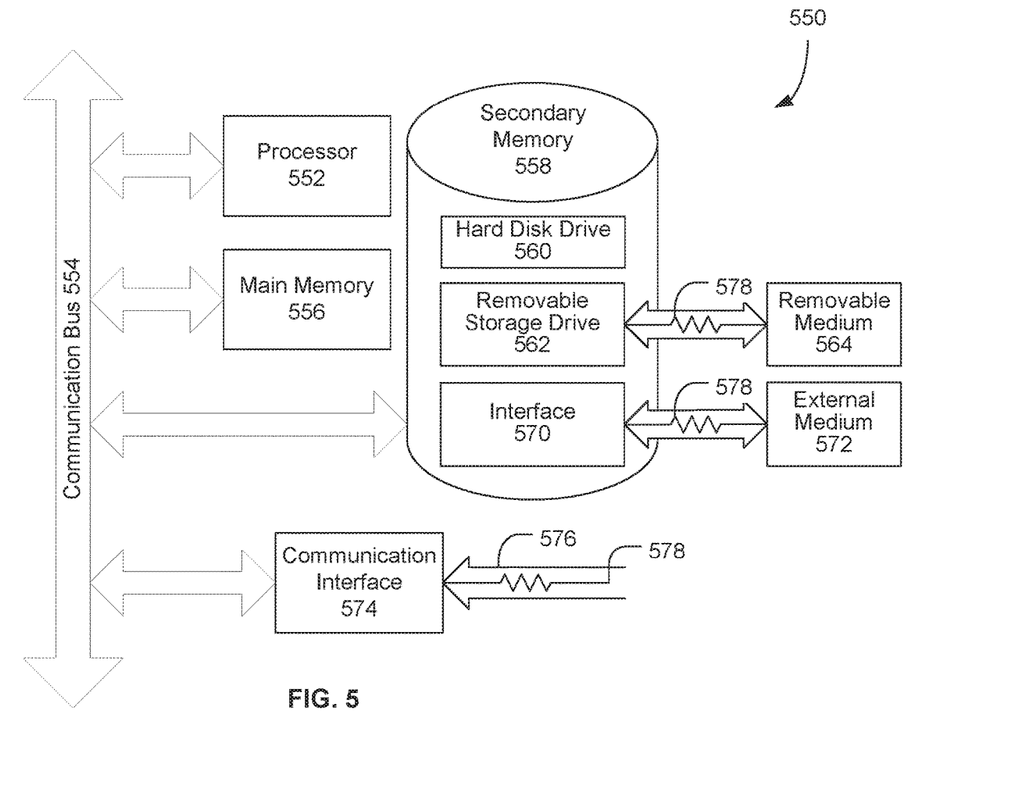
FIG. 5 is a block diagram illustrating an example computer system that may be used in connection with various embodiments described herein.

FIG. 5 is a block diagram illustrating an example computer system 550 that may be used in connection with various embodiments described herein. For example, the computer system 550 may be used in conjunction with the referral source, scanning center, or consultant previously described with respect to FIG. 1. However, other computer systems and/or architectures may be used, as will be clear to those skilled in the art.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 is preferably connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPM"), IEEE 696/S-100, and the like.

Computer system 550 preferably includes a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564 in a well-known manner. Removable storage medium 564 may be, for example, a floppy disk, magnetic tape, CD, DVD, etc.

The removable storage medium 564 is preferably a computer readable medium having stored thereon computer executable code (i.e., software) and/or data. The computer software or data stored on the removable storage medium 564 is read into the computer system 550 as electrical communication signals 578.

In alternative embodiments, secondary memory 558 may include other similar means for allowing computer programs or other data or instructions to be loaded into the computer system 550. Such means may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 574 are generally in the form of electrical communication signals 578. These signals 578 are preferably provided to communication interface 574 via a communication channel 576. Communication channel 576 carries signals 578 and can be implemented using a variety of wired or wireless communication means including wire or cable, fiber optics, conventional phone line, cellular phone link, wireless data communication link, radio frequency (RF) link, or infrared link, just to name a few.

Computer executable code (i.e., computer programs or software) is stored in the main memory 556 and/or the secondary memory 558. Computer programs can also be received via communication interface 574 and stored in the main memory 556 and/or the secondary memory 558. Such computer programs, when executed, enable the computer system 550 to perform the various functions of the present invention as previously described.

In this description, the term "computer readable medium" is used to refer to any media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These computer readable mediums are means for providing executable code, programming instructions, and software to the computer system 550.

In an embodiment that is implemented using software, the software may be stored on a computer readable medium and loaded into computer system 550 by way of removable storage drive 562, interface 570, or communication interface 574. In such an embodiment, the software is loaded into the computer system 550 in the form of electrical communication signals 578. The software, when executed by the processor 552, preferably causes the processor 552 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A system comprising:
a memory; and
at least one hardware processor of a server, the at least one hardware processor coupled to the memory and configured to:
at a first time, receive metadata for a digital slide image from a source computer over at least one network, the digital slide image comprising an image of a specimen, wherein the metadata comprises reference information regarding a location of the digital slide image stored in the source computer,
at a second time after the first time, use the reference information of the metadata to facilitate remote viewing, via the server, of the digital slide image stored in the source computer, wherein the remote viewing comprises rendering of at least a portion of the digital slide image at a remote computer,
at a third time after the second time, receive the digital slide image from the source computer over the at least one network, wherein the third time is associated with a lower usage of the at least one network's bandwidth than the second time,
store a copy of the digital slide image in the memory, and
provide access to at least a portion of the stored copy of the digital slide image to the remote computer over the at least one network for analysis.

2. The system of claim 1, wherein the at least one hardware processor is further configured to store a profile for each of a plurality of remote computers, wherein each of the profiles comprises one or more references to one or more digital slide images previously analyzed at the corresponding remote computer.

3. The system of claim 1, wherein the at least one hardware processor is further configured to select the remote computer from among a plurality of remote computers.

4. The system of claim 1, wherein providing access to at least a portion of the stored copy of the digital slide image comprises:
providing access to the at least a portion of the stored copy of the digital slide image to a first remote computer; and
after expiration of a time period since providing the access to the first remote computer without receiving an analysis of the stored copy of the digital slide image from the first remote computer, revoking the access from the first remote computer, and providing access to the at least a portion of the stored copy of the digital slide image to a second remote computer that is different than the first remote computer.

5. The system of claim 1, wherein providing access to at least a portion of the stored copy of the digital slide image comprises providing access to the at least a portion of the stored copy of the digital slide image to two or more remote computers, and wherein the at least one hardware processor is further configured to engage, for analysis of the digital slide image, a first one of the two or more remote computers to respond to the providing of the access to the at least a portion of the stored copy of the digital slide image.

6. The system of claim 1, wherein the at least one hardware processor is further configured to send access information for accessing the stored copy of the digital slide image to the remote computer, wherein the access information comprises a link for accessing the stored copy of the digital slide image at the server.

7. The system of claim 1, wherein the at least one hardware processor is further configured to:
   receive the analysis from the remote computer; and
   provide the analysis to the source computer.
8. The system of claim 1, wherein the at least one hardware processor is further configured to:
   initiate an audio-visual conference between the source computer and remote computer; and
   during the audio-visual conference,
      provide at least a portion of the stored copy of the digital slide image to both a display of the source computer and a display of the remote computer,
      receive an annotation associated with the at least a portion of the stored copy of the digital slide image from the remote computer, and
      propagate the annotation to the display of the source computer.
9. The system of claim 8, wherein the at least one hardware processor is further configured to:
   record the audio-visual conference; and
   associate the recorded audio-visual conference with a medical file associated with the specimen.
10. The system of claim 1, wherein the at least one hardware processor is further configured to:
    process the digital slide image to generate a cell count; and
    provide the cell count to the remote computer.
11. The system of claim 1, wherein a size of the digital slide image is at least a plurality of gigabytes.
12. The system of claim 1, wherein the third time occurs during off-peak network usage hours.
13. A method comprising:
    at a hardware processor of a server, at a first time, receiving metadata for a digital slide image from a source computer over at least one network, the digital slide image comprising an image of a specimen, wherein the metadata comprises reference information regarding a location of the digital slide image stored in the source computer;
    at a second time after the first time, using the reference information of the metadata to facilitate remote viewing, via the server, of the digital slide image stored in the source computer, wherein the remote viewing comprises rendering of at least a portion of the digital slide image at a remote computer;
    at the server, at a third time after the second time, receiving the digital slide image from the source computer over the at least one network, wherein the third time is associated with a lower usage of the at least one network's bandwidth than the second time;
    storing a copy of the digital slide image in a memory at the server; and
    at the server, providing access to at least a portion of the stored copy of the digital slide image to a remote computer over the at least one network for analysis.

14. The method of claim 13, further comprising storing a profile for each of a plurality of remote computers, wherein each of the profiles comprises one or more references to one or more digital slide images previously analyzed at the corresponding remote computer.
15. The method of claim 13, further comprising selecting the remote computer from among a plurality of remote computers.
16. The method of claim 13, wherein providing access to at least a portion of the stored copy of the digital slide image comprises:
    providing access to the at least a portion of the stored copy of the digital slide image to a first remote computer; and
    after expiration of a time period since providing the access to the first remote computer without receiving an analysis of the stored copy of the digital slide image from the first remote computer, revoking the access from the first remote computer, and providing access to the at least a portion of the stored copy of the digital slide image to a second remote computer that is different than the first remote computer.
17. The method of claim 13, wherein providing access to at least a portion of the stored copy of the digital slide image comprises providing access to the at least a portion of the stored copy of the digital slide image to two or more remote computers, and wherein the method further comprising engaging, for analysis of the digital slide image, a first one of the two or more remote computers to respond to the providing of the access to the at least a portion of the stored copy of the digital slide image.
18. The method of claim 13, further comprising sending access information for accessing the stored copy of the digital slide image to the one or more remote computers, wherein the access information comprises a link for accessing the stored copy of the digital slide image at the server.
19. The method of claim 13, further comprising:
    receiving the analysis from the remote computer; and
    providing the analysis to the source computer.
20. The method of claim 13, further comprising:
    initiating an audio-visual conference between the source computer and remote computer; and
    during the audio-visual conference,
       providing at least a portion of the stored copy of the digital slide image to both a display of the source computer and a display of the remote computer,
       receiving an annotation associated with the at least a portion of the stored copy of the digital slide image from the remote computer, and
       propagating the annotation to the display of the source computer.
21. The method of claim 20, further comprising:
    recording the audio-visual conference; and
    associating the recorded audio-visual conference with a medical file associated with the specimen.

* * * * *

UNITED STATES PATENT AND TRADEMARK OFFICE
CERTIFICATE OF CORRECTION

| | | |
|---|---|---|
| PATENT NO. | : 11,211,170 B2 | Page 1 of 1 |
| APPLICATION NO. | : 15/912428 | |
| DATED | : December 28, 2021 | |
| INVENTOR(S) | : Dirk G. Soenksen | |

It is certified that error appears in the above-identified patent and that said Letters Patent is hereby corrected as shown below:

In the Specification

Column 9, Line 19, delete "("GPM")," and insert -- ("GPIB"), --.

Signed and Sealed this
Fifth Day of July, 2022

Katherine Kelly Vidal
*Director of the United States Patent and Trademark Office*